US006664443B1

(12) United States Patent
Hutton et al.

(10) Patent No.: US 6,664,443 B1
(45) Date of Patent: Dec. 16, 2003

(54) PATHOGENIC TAU MUTATIONS IN TRANSGENIC MICE

(75) Inventors: Michael L. Hutton, Jacksonville, FL (US); Jada M. Lewis, Jacksonville, FL (US); Eileen M. McGowan, Jacksonville, FL (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 09/628,608

(22) Filed: Jul. 31, 2000

Related U.S. Application Data

(63) Continuation-in-part of application No. 09/302,964, filed on Apr. 30, 1999, now Pat. No. 6,475,723.
(60) Provisional application No. 60/097,492, filed on Aug. 21, 1998, provisional application No. 60/087,942, filed on Jun. 4, 1998, and provisional application No. 60/083,791, filed on May 1, 1998.

(51) Int. Cl.$^7$ ...................... A01K 67/00; A01K 67/027; G01N 33/00; C12P 21/100; C12N 15/00

(52) U.S. Cl. .............................. 800/12; 800/3; 800/4; 800/8; 800/9; 800/14; 800/18; 800/22

(58) Field of Search ............................... 800/3, 4, 8, 9, 800/14, 18, 22

(56) References Cited

U.S. PATENT DOCUMENTS

| | | | |
|---|---|---|---|
| 4,873,191 A | 10/1989 | Wagner et al. | |
| 5,455,169 A | 10/1995 | Mullan | |
| 5,877,399 A | 3/1999 | Hsiao et al. | |
| 5,958,684 A | 9/1999 | Van Leeuwen | |

FOREIGN PATENT DOCUMENTS

| | | |
|---|---|---|
| WO | WO 97/27296 | 7/1997 |
| WO | WO 97/48792 | 12/1997 |
| WO | WO 98/01549 | 1/1998 |
| WO | WO 98/17782 | 4/1998 |

OTHER PUBLICATIONS

Wall et al.; Transgenic Dairy Cattle: Genetic Engineering on a Large Scale, 1996, J. Dairy Sci.: 2213–2224.*
Mullins et.al.; Perspectives Series: Molecular Medicine in Genetically Engineered Animals, 1996, J. Clin. Invest., vol. 97, No. 7:1557–1560.*
Hammer et.al.; Genetic Engineering of Mammalian Embryos, 1986, J. Anim. Sci. 63: 269–278.*
Ebert et.al.; A Moloney MLV–Rat Somatotropin Fusion Gene Produces Biologically Acitve Somatotropin in a Transgenic Pig, 1988, Mol. Endocrinal 3: 277–283.*
Conrad et.al.; Genetic Evidence for the Involvement of in Progressive Supranuclear Palsy, 1997, American Neurological Association: 277–281.*
Roks et.al.; Mutation screening of the tau gene in patients with early–onset Alzheimer's disease, 1999, Neuroscience Letters 277: 137–139.*
Accession No. CAA32636, 1993.*
Accession No. AAA60615, 1995.*
Accession No. AAC04277, 1998.*
Accession No. AAC04279., 1998.*
Andreadis et al., *Biochemistry*, 1992, 31(43):10626–10633.
Arrasate et al., *FEBS Letters*, 1999, 446:199–202.
Baker et al., *Ann. Neurol.*, 1997, 42(5):794–798.
Baker et al., *Human Mol. Genet.*, 1999, 8(4):711–715.
Borchelt et al., *Genet. Anal.*, 1996, 13:159–163.
Cibelli et al., *Science*, 1998, 280:1256–1258.
Conrad et al., *Ann. Neurology*, 1997, 41(2):277–281.
Dayanandan et al., *FEBS Letters*, 1999, 466:228–232.
Dickson et al., *Acta Neuropathol.*, 1993, 85:463.
Dickson, *Ann. Neurol.*, 1997, 42:541–544.
Ebert et al., *Mol. Endocrinol.*, 1988, 2(3):277–283.
Foster et al., *Ann. Neurol.*, 1997, 41(6):706–715.
Froleich et al., *Am. J. Med. Genet.*, 1997, 74:380–385.
Gravina et al., *J. Biol. Chem.*, 1995, 270:7013.
Greenberg and Davies, *Proc. Natl. Acad. Sci. USA*, 1990, 87:5827–5831.
Greenberg et al., *J. Biol. Chem.*, 1992, 267:564–569.
Hammer et al., *J. Animal Sci.*, 1986 63(1):269–278.
Heutink et al., *Ann. Neurol.*, 1997, 41(2):150–159.
Hsiao et al., *Science*, 1996, 274:99.
Hutton et al., *Nature*, 1998, 393:702–705.
Ingelson et al., *Neuroscience Letters*, 1996, 220:9–12.
Iqbal et al., *Neurobiol. Aging*, 1991, 12:357–361.
Jicha et al., *J. Neurosci. Res.*, 1997, 48:128–132.
Jicha et al., *J. Neurosci. Res.*, 1999, 55:713–723.
Leger et al., *J. Biol. Chem.*, 1997, 272(13):8441–8446.
Lo, *Mol. Cell. Biol.*, 1983, 3:1803.
Mirra et al., *J. Neuropath. Exp. Neurol.*, 1999, 58(4):335–345.
Mullan et al., *Nature Gen.*, 1992, 1:345–347.
Mullins et al., *J. Clin. Inves.*, 1996, 87(7):1557–1560.
Murrell et al., *Am. J. Hum. Genet.*, 1997, 61(5):1131–1138.
Reed et al., *Ann. Neurol.*, 1997, 42(4):564–572.
Roks et al., *Neuroscience Letters*, 1999, 277(2):137–139.
Schweers et al., *Proc. Natl. Acad. Sci. USA*, 1995, 92:8463–8467.
Spillantini et al., *Brain Pathology*, 1998, 8(2):387–402.
Thompson et al., *Cell*, 1989, 56:313.
Trojanowski and Lee, *Brain Pathol.*, 1999, 9:733–739.
Van der Putten et al., *Proc. Natl. Acad. Sci. USA*, 1985, 82:6148.
Wagner et al., *J. Cell Sci.*, 1996, 109:1537–1543.
Wakayama et al., *Nature*, 1998, 394:369–374.
Wall et al., *J. Dairy Sci.*, 1997, 80:2213–2224.
Wilmut et al., *Nature*, 1997, 385(6619):810–813.

\* cited by examiner

*Primary Examiner*—Deborah Crouch
*Assistant Examiner*—Joseph Woitach
(74) *Attorney, Agent, or Firm*—Fish & Richardson P.C., P.A.

(57) ABSTRACT

Isolated nucleic acid molecules that include a tau gene sequence are described. The tau gene sequences have a mutation linked to a Tau pathology. Transgenic non-human mammals that develop a Tau pathology also are described.

17 Claims, 5 Drawing Sheets

- 270 bp
- 177 bp

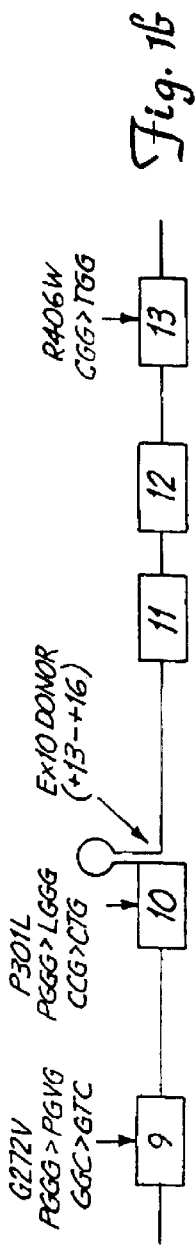
Fig. 1b
Fig. 1c
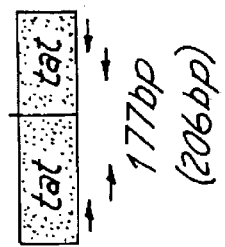
Fig. 3A
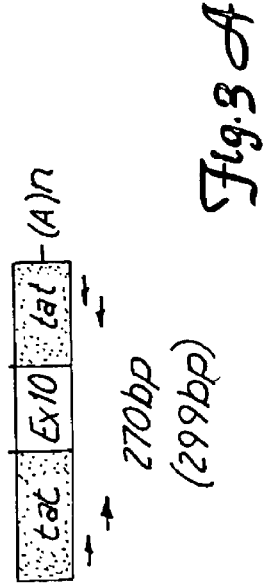

PATHOGENIC TAU MUTATIONS IN TRANSGENIC MICE

CROSS REFERENCE TO RELATED APPLICATIONS

This application is a continuation-in-part of U.S. Ser. No. 09/302,964, filed Apr. 30, 1999, now U.S. Pat. No. 6,476,723 which claims priority from U.S. Provisional Application Serial No. 60/097,492, filed Aug. 21, 1998, U.S. Provisional Application Serial No. 60/087,942, filed Jun. 4, 1998, and U.S. Provisional Application Serial No. 60/083,791, filed May 1, 1998.

STATEMENT AS TO FEDERALLY SPONSORED RESEARCH

Funding for the work described herein was provided in part by the Federal government, which has certain rights in the invention.

TECHNICAL FIELD

The invention relates to transgenic non-human mammals that develop Tau pathologies.

BACKGROUND

Frontotemporal dementia and parkinsonism linked to chromosome 17 (FTDP-17) is characterized clinically by behavioral, cognitive, and motor disturbance. Historically, many cases of this disease have been described as Pick's disease. In the majority of families described to date, personality change is the presenting symptom, with initial behavioral changes accompanied by progressive cognitive impairment and sometimes parkinsonism. At autopsy, all patients with FTDP-17 display pronounced fronto-temporal atrophy and neuronal cell loss, gray and white matter gliosis, and superficial cortical spongiform changes. More variably, ballooned neurons, or Pick's cells, are present. In addition, most FTDP-17 cases show neuronal and/or glial inclusions that stain positively with antibodies raised against the microtubule associated protein Tau, although the Tau pathology varies considerably in both its quantity (or severity) and characteristics. Patients with FTDP-17 do not have Lewy bodies or, crucially, Pick bodies, which distinguishes them from classical Pick's disease cases. The disease is inherited as an autosomal dominant trait with age dependent penetrance. The age of onset can be highly variable but is usually between the ages of 45–65 years.

SUMMARY

The invention is based on the discovery of mutations in the tau gene that are linked to Tau pathologies. Thus, the invention provides nucleic acid molecules that include such mutations, allowing animal models of neurodegenerative diseases to be developed. Identification of the mutations also provides methods for determining a diagnosis of neurodegenerative disease in a patient.

The invention features an isolated nucleic acid molecule including a tau gene sequence, wherein the molecule has a mutation linked to a Tau pathology. The nucleic acid molecule can be from about 15 nucleotides in length to full-length. The mutation can be located in an exon or in an intron. A mutation can be in exon 7, exon 9, exon 10, or in exon 13, and in particular embodiments, at a region encoding amino acids 152, 257, 272, 301, 389, or 406. In one embodiment, the mutation at amino acid 152 is a change from an alanine to a threonine residue, the mutation at amino acid 257 is a change from a lysine to a threonine residue, and the mutation at amino acid 272 is a change from a glycine residue to a valine residue. The mutation at amino acid 301 can be a change from a proline residue to a leucine residue. The mutation at amino acid 389 can be a change from a glycine to an arginine residue. The mutation of amino acid 406 can be a change from an arginine to a tryptophan residue. An additional mutation can include deletion of amino acid 280. The mutation also can be in a splice donor site region and, in a particular embodiment, can destabilize a stem-loop structure of the splice donor site region and can be in a region 13–16 nucleotides 3' of the exon 10 splice donor site.

The invention also features an isolated polypeptide encoded by a tau nucleic acid molecule of the invention. The polypeptide contains a mutation linked to a Tau pathology. Suitable mutations are described above.

In another aspect, the invention features a transgenic non-human mammal including a nucleic acid construct and progeny thereof. The nucleic acid construct includes a regulatory element such as a brain-specific promoter (e.g., a prion gene promoter) operably linked to a nucleic acid sequence encoding a Tau polypeptide (e.g., a human Tau polypeptide). The Tau polypeptide includes a pathogenic Tau mutation and is expressed in the transgenic non-human mammal. The transgenic non-human mammal exhibits a Tau pathology (e.g., the non-human mammal develops neurofibrillary tangles), and can be a rodent such as a mouse. The mutation can be at amino acid 152, 257, 272, 280, 301, 389, or 406 of the human Tau polypeptide, e.g., substitution of a leucine residue for a proline residue at amino acid 301.

The transgenic non-human mammal further can include a nucleic acid construct that includes a regulatory element operably linked to a nucleic acid molecule encoding a human amyloid precursor protein (APP) or a human presenilin-1 protein. The human APP can include mutations at amino acids 670 and 671 e.g., substitution of an asparagine residue at amino acid 670 and substitution of a leucine residue at amino acid 671. Transgenic non-human mammals expressing a human APP and a tau polypeptide can develop neurofibrillary tangles and amyloid plaques. Such non-human mammals exhibit an increased number of neurofibrillary tangles as compared with a control transgenic non-human mammal expressing a mutant Tau polypeptide.

In another aspect, the invention features a method for identifying agents that inhibit development of a Tau pathology. The method includes administering a test agent to a transgenic non-human mammal and determining if the test agent inhibits development of the Tau pathology in the transgenic non-human mammal as compared with a corresponding transgenic non-human mammal to which the test agent has not been administered. The transgenic non-human mammal includes a nucleic acid construct, wherein the construct includes a regulatory element operably linked to a nucleic acid molecule encoding a Tau polypeptide, wherein the polypeptide includes a pathogenic Tau mutation and is expressed in the transgenic non-human mammal, and wherein the transgenic non-human mammal exhibits a Tau pathology. The mutation can be at amino acid 152, 257, 272, 280, 301, 389, or 406, as described above. The transgenic non-human mammal can develop neurofibrillary tangles.

Transgenic non-human mammal useful in the method also can express a human APP or human presenilin-1 polypeptide. Human APP can have a mutation at amino acids 670 and 671, e.g., an asparagine residue can be substituted at amino acid 670 and a leucine residue can be substituted at amino acid 671. Such a transgenic non-human mammal can develop neurofibrillary tangles and amyloid plaques. The transgenic non-human mammal can develop an increased number of neurofibrillary tangles as compared with a control transgenic non-human mammal expressing a mutant Tau polypeptide.

The invention also relates to a method for determining a diagnosis, prognosis, or risk of neurodegenerative disease in a patient. The method includes detecting a tau gene mutation in genomic DNA of the patient, wherein the mutation is linked to a Tau pathology. Mutations that are linked to Tau pathologies are described above.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIGS. 1A–1C are a segregation analysis (A), a schematic representation (B), and a sequence alignment (C) of tau mutations in FTDP-17. FIG. 1A is a segregation analysis of the exon 10 splice donor +16 mutation in the AusI kindred. The presence of the mutation is indicated by an extra band at 148 bp on the agarose gel, while the normal allele is represented by a band at 200 bp. Individual III.6 has the mutation and the disease haplotype despite being currently unaffected. FIG. 1B is a schematic representation of the tau gene (exons 9–13) displaying the relative locations of missense mutations in the coding region and in the splice donor site. The effect of two missense mutations, G272V and P301L, on the PGGG motif in the microtubule binding domains encoded by exon 9 and 10, respectively, is shown. FIG. 1C is a sequence alignment of the microtubule binding domain encoded by exon 10 with the equivalent regions from mouse and cow and from the human and rat microtubule associated protein 4 (MAP4). The location of the P301L missense mutation is indicated above the alignment.

FIGS. 3A and 3B are a schematic representation of major RT-PCR products generated by exon trapping analysis of tau exon 10 (A) and results of exon trapping analysis of tau exon 10 (B).

DETAILED DESCRIPTION

Tau Mutations

Figure 1A:
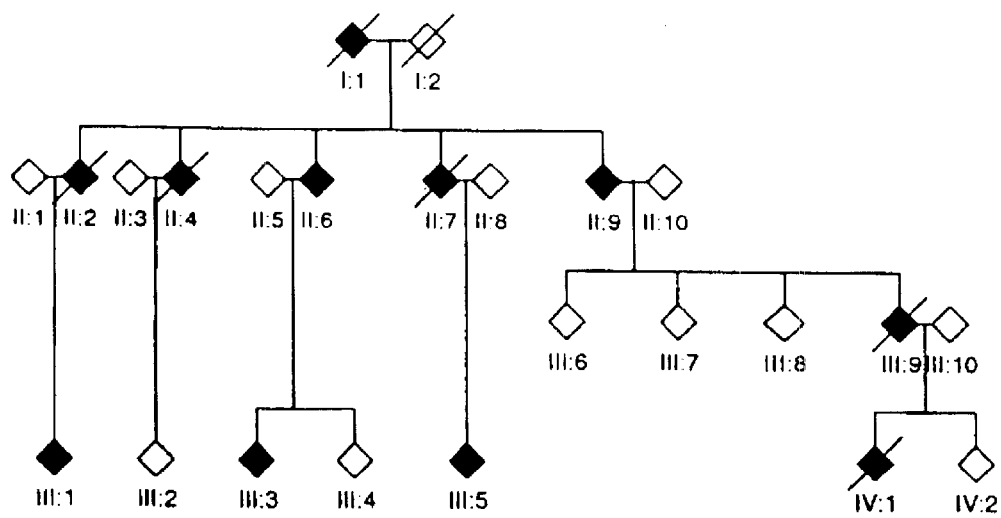
Figure 1A:

In one aspect, the invention features an isolated nucleic acid molecule including a tau gene sequence, wherein the nucleic acid molecule has at least one mutation linked to a Tau pathology. As used herein, "isolated" refers to a sequence corresponding to part or all of the tau gene, but free of sequences that normally flank one or both sides of the tau gene in a mammalian genome. An isolated nucleic acid molecule can be, for example, a recombinant DNA molecule, provided one of the nucleic acid sequences normally found flanking that recombinant DNA molecule in a naturally-occurring genome is removed or absent. Thus, isolated nucleic acid molecules include, without limitation, a recombinant DNA that exists as a separate molecule (e.g., a cDNA or genomic DNA fragment produced by PCR or restriction endonuclease treatment) independent of other sequences as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated nucleic acid molecule can include a recombinant DNA molecule that is part of a hybrid or fusion nucleic acid molecule.

It will be apparent to those of skill in the art that a nucleic acid molecule existing among hundreds to millions of other nucleic acid molecules within, for example, cDNA or genomic libraries, or gel slices containing a genomic DNA restriction digest is not to be considered an isolated nucleic acid molecule.

A nucleic acid molecule of the invention typically is at least 15 nucleotides in length. For example, the nucleic acid molecule can be about 15 to 20, 20–50, 50–100, or 100–500 nucleotides in length. In other embodiments, the nucleic acid is full-length. The nucleic acid molecules can be in the form of RNA or in the form of DNA. The DNA can be double-stranded or single-stranded, circular or linear, and can be either coding or non-coding.

As used herein, "Tau pathology" refers to neurofibrillary tangles observed in brain, including one or more of the following: paired helical filaments (PHFs), straight Tau filaments, and any other type of Tau filament. Tau pathology also includes neuronal and/or glial inclusions or insoluble deposits that stain positively with anti-Tau antibodies. The tau gene encodes the microtubule associated protein Tau that is present in abnormal inclusions seen in FTDP-17 and is also the major component of the PHFs that make up the characteristic tangles seen in Alzheimer's disease (AD) and other neurodegenerative disorders. The human Tau protein found in brain is encoded by eleven exons. The sequence of the wild-type human tau gene is described by Andreadis, A. et al., *Biochemistry*, 31(43):10626–10633 (1992). The gene undergoes alternative splicing with exons 2, 3, and 10 absent from some forms of the mature brain tau mRNA. A total of six different tau mRNAs is generated as a result of this alternative splicing, with the mRNAs encoding proteins of 352–441 amino acids. The alternative splicing of exon 10 generates Tau protein with either three or four microtubule binding motifs that each are imperfect repeats of 31 or 32 residues. Tau protein containing three microtubule binding motifs is referred to herein as the three-repeat isoform, whereas Tau protein containing four microtubule binding motifs is referred to herein as the four-repeat isoform. Tau proteins containing three microtubule binding motifs (exon 10 −) form paired helical filaments, similar to those seen in the brains of AD patients, during in vitro aggregation experiments, while Tau proteins containing four microtubule binding motifs (exon 10 +) form straight filaments.

The FTDP-17 locus maps to a 2 cM region on chromosome 17q21.1. As described herein, analysis of a large number of families with FTDP-17 and analysis of coding and non-coding regions of the tau gene revealed mutations linked to FTDP-17. The 11 tau coding exons and flanking intronic regions were initially sequenced in 38 individuals from families with fronto-temporal dementia from Scandinavia (9 families), the Netherlands (2 families), the USA (4 families), Australia (1 family), and from the Greater Manchester area of the UK (22 families). In this group, 7 families had previously displayed evidence for linkage to chromosome 17. The sequence analysis of the tau gene identified mutations in 5 of 7 families in which linkage to chromosome 17 had previously been indicated.

Mutations that are linked to Tau pathologies can be detected, for example, in exon 7, exon 9, exon 10, and exon 13. Amino acid mutations described herein are numbered from the longest Tau isoform, starting with the initial methionine. Amino acids have been designated herein by standard one letter and three letter abbreviations. Nucleotide mutations that correspond with the Tau amino acid mutations described herein are numbered from the cDNA encoding the longest Tau isoform. Nucleotides have been designated by standard one letter abbreviations. Table 1 provides examples of Tau mutations that are linked to Tau pathologies, and the corresponding changes in nucleotide sequence. Other nucleotide sequences leading to the same amino acid changes can be ascertained from the known degeneracy of the genetic code.

TABLE 1

| Amino Acid Mutation | Corresponding Nucleotide Mutation |
|---|---|
| A152T | G454A |
| K257T | A770C |
| G272V | G815T |
| ΔK280 | ΔAAG(838–840) |
| P301L | C902T |
| G389R | G1166A |
| R406W | C1216T |

In exon 7, the mutation can include a change from an alanine to a threonine at residue 152 (i.e., A152T), which can result from a change at nucleotide 454 of a guanine to an adenine (i.e., G454A) in the tau gene sequence. A mutation in exon 9 from a lysine to a threonine at amino acid 257 (K257T) can result from a change of an adenine to a cytosine at nucleotide 770 of the tau gene sequence. Amino acid 272 can be changed from a glycine residue to a valine residue (G272V), a highly conserved residue within the microtubule binding domain encoded by exon 9, and is found in all Tau isoforms. The G272V mutation can result from a change of a thymine to a guanine at nucleotide 815 of the tau gene sequence. Amino acid 389 can be changed from a glycine to an arginine residue (G389R) in exon 13, with a corresponding change from a guanine to an adenine at nucleotide 1166. Amino acid 406, a highly conserved residue near the carboxy terminus of Tau, can be changed from an arginine to a tryptophan residue (R406W), with a corresponding change from a cytosine to a thymine at nucleotide 1216 of the tau gene.

Amino acid 301 can be changed from a proline residue to a leucine residue (P301L) in exon 10. The P301L substitution is a non-conservative substitution that occurs in a highly conserved region of the Tau protein sequence within one of the microtubule-binding domains. A proline residue is observed at the equivalent position in all species from which Tau has been cloned (see FIG. 1C). As a result, this substitution is highly likely to disrupt Tau microtubule binding. The P301L substitution only affects the four-repeat isoform, however, as exon 10 is spliced out of the mRNA that encodes the three-repeat exon 9–12 isoform.

Figure 2A:
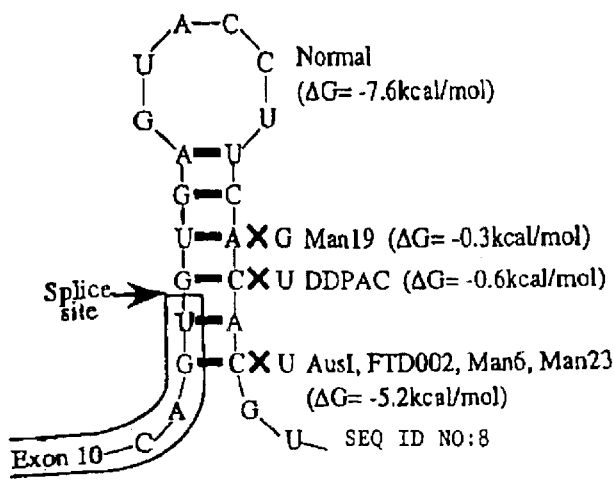
FIGS. 2A and 2B contain the sequence of the exon 10 splice donor site shown in a predicted stem-loop structure (A) and in linear form (B). The positions of three mutations are marked and the predicted free energy of the stem-loop with and without mutations is indicated. Predicted binding of the U1 SnRNP binding is thought to be blocked by the formation of the stem-loop.
Figure 2B:
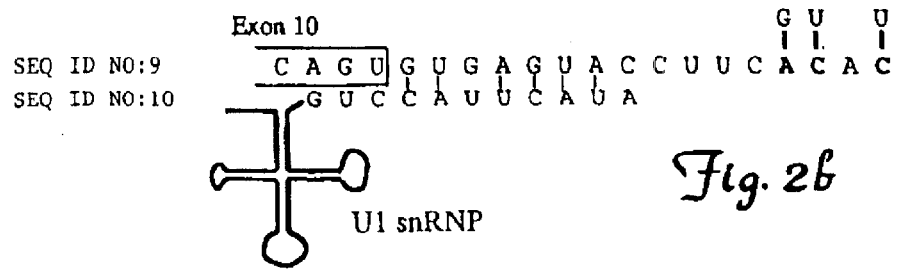

A deletion of amino acid 280 was detected in a single Dutch family, with corresponding nucleotides 838–840 deleted from the tau gene sequence. In addition, mutations were detected in the exon 10 splice donor site region. For example, heterozygous mutations were identified in a cluster of four nucleotides 13–16 bp 3' of the exon 10 donor splice site (FIG. 2). No mutations were found in the tau gene in two families (HDDD2 and HFTD3).

The mutations described herein appear to cause FTDP-17, one of the major autosomal dominant loci associated with neurodegeneration. These data also indicate that a tau gene variant (V337M) in a family with FTDP-17 (Seattle A), Spillantini, M. G. et al., *Brain Path.*, 8:387–402 (1998), is likely pathogenic. The previous absence of mutations in other families had led to the suggestion that this might be a benign polymorphism. Most importantly, the identification of pathogenic missense and splice donor site mutations associated with FTDP-17 demonstrates for the first time that Tau dysfunction can lead to neurodegeneration. In addition, the nature of the splice-donor site mutations indicates that the relative levels of four-repeat and three-repeat Tau proteins are crucial to the correct functioning of Tau, at least in the brain. This is consistent with the observation that alternative splicing of exon 10 is known to be developmentally regulated. These mutations, by affecting the potential stem-loop structure in the exon 10 donor site, also reveal at least part of the mechanism by which alternative splicing of this exon is regulated. The existence of splice donor site, deletion, and missense mutations also may partially explain the variability observed in soluble Tau protein in FTDP-17.

The mutations in the exon 10 splice donor site are expected to lead to an increase in alternative splicing. A putative stem-loop structure containing a 12 base pair stem and a 6 base pair loop (FIG. 2A) spans the exon 10 splice donor site. All 3 of the mutations identified in this region occurred within the "stem" of this structure and would be expected to destabilize it. Short stem-loop structures can potentially sequester splice-donor sites and lead to alternative splice-donor site usage. Thus, the formation of the stem-loop structure might be involved in the regulation of exon 10 alternative splicing by blocking or slowing the use of this donor site, permitting the splicing of exon 9 to exon 11, and the generation of tau transcripts lacking exon 10. The result would be the maintenance of a precise ratio of transcripts with and without exon 10, and in turn, this would determine the ratio of four-repeat to three-repeat Tau protein. The mutations within the stem-loop associated with FTDP-17 are thought to destabilize this structure, promoting the use of the donor site and the inclusion of exon 10 in tau mRNA. This proposed mechanism would predict an increase in the proportion of tau transcripts containing exon 10 and thus an increase in the ratio of four-repeat to three-repeat protein isoforms. This mechanism for these mutations is consistent with the observation that soluble Tau in at least one FTDP-17 family displays a relative preponderance of Tau isoforms with four-repeats compared to control brains. In addition, the absence of this type of splice site mutation in many families (including those with missense mutations) is consistent with the observation that in other FTDP-17 families, the relative abundance of Tau isoforms with three- and four-repeats is similar to that seen in control brains.

Transgenic Non-human Mammals

The invention also features a transgenic non-human mammal including a nucleic acid construct. As used herein, "transgenic non-human mammal" includes the founder transgenic non-human mammals as well as progeny of the founders. The nucleic acid construct includes a regulatory element operably linked to a nucleic acid sequence encoding a Tau polypeptide. Nucleic acid constructs can be produced through standard recombinant DNA techniques. As used herein, "Tau polypeptide" refers to a Tau polypeptide of any length. Expression of the Tau polypeptide is linked to a Tau pathology in the transgenic non-human mammals. The Tau polypeptide can be, for example, encoded by a portion of an exon, a complete exon, or the full-length tau cDNA, and can be wild-type or can contain at least one mutation. Particularly useful mutations are described above.

Regulatory elements provide expression of the Tau polypeptide in sufficient levels to produce a Tau pathology. Regulatory elements include, for example, promoters, enhancers, inducible elements, and other upstream promoter elements. In particular embodiments, a regulatory element provides enhanced expression of the Tau polypeptide in the brain. A variety of regulatory elements can be used to control expression of the Tau polypeptide. Non-limiting examples include the metallothionine promoter, the rat neural-specific enolase promoter, the human β-actin gene promoter, the human platelet derived growth factor B chain promoter, the rat sodium channel gene promoter, the human copper-zinc superoxide dismutase gene promoter, and the prion gene promoter (e.g., from mouse or hamster).

Transgenic non-human mammals can be farm animals such as pigs, goats, sheep, cows, horses, and rabbits, rodents such as rats, guinea pigs, and mice, and non-human primates such as baboons, monkeys, and chimpanzees. Transgenic mice are particularly useful.

Various techniques known in the art can be used to introduce nucleic acid constructs into non-human mammals to produce the founder lines of the transgenic non-human mammals, in which the nucleic acid construct is integrated into the genome. Such techniques include, but are not limited to, pronuclear microinjection (U.S. Pat. No. 4,873, 191), retrovirus mediated gene transfer into germ lines (Van der Putten et al., *Proc. Natl. Acad. Sci. USA*, 82:6148, 1985), gene targeting into embryonic stem cells (Thompson et al., *Cell*, 56:313, 1989), electroporation of embryos (Lo, *Mol. Cell. Biol.*, 3:1803, 1983), and transformation of somatic cells, such as cumulus or mammary cells in vitro followed by nuclear transplantation (Wilmut et al., *Nature*, 385(6619) :810–813, 1997; and Wakayama et al., *Nature*, 394:369–374, 1998). For example, fetal fibroblasts can be genetically modified such that they express a Tau polypeptide, then fused with enucleated oocytes. After activation of the oocytes, the eggs are cultured to the blastocyst stage. See, for example, Cibelli et al., *Science*, 280:1256–1258 (1998).

Once transgenic non-human mammals have been generated, expression of the Tau polypeptide can be assessed using standard techniques. Initial screening can be accomplished by Southern blot analysis or polymerase chain reaction (PCR) techniques to determine whether or not integration of the transgene has taken place. See, for example, sections 9.37–9.52 of Sambrook et al., 1989, "*Molecular Cloning, A Laboratory Manual*", second edition, Cold Spring Harbor Press, Plainview, N.Y., for a description of Southern analysis. Standard breeding techniques can be used to create animals homozygous for the tau transgene from the initial heterozygous founder animals.

PCR refers to a procedure or technique in which target nucleic acids are amplified. Generally, sequence information from the ends of the region of interest or beyond is employed to design oligonucleotide primers that are identical or similar in sequence to opposite strands of the template to be amplified. PCR can be used to amplify specific sequences from DNA as well as RNA, including sequences from total genomic DNA or total cellular RNA. Primers are typically 14 to 40 nucleotides in length, but can range from 10 nucleotides to hundreds of nucleotides in length. PCR is described, for example in *PCR Primer: A Laboratory Manual*, Ed. by Dieffenbach, C. and Dveksler, G., Cold Spring Harbor Laboratory Press, 1995. Nucleic acids also can be amplified by ligase chain reaction, strand displacement amplification, self-sustained sequence replication, or nucleic acid sequence-based amplified. See, for example, Lewis, R. *Genetic Engineering News*, 12(9):1 (1992); Guatelli et al., *Proc. Natl. Acad. Sci. USA*, 87:1874–1878 (1990); and Weiss, R., *Science*, 254:1292 (1991).

Expression of the nucleic acid sequence encoding a Tau polypeptide in the tissues of the transgenic non-human mammals can be assessed using techniques that include, but are not limited to, Northern blot analysis of tissue samples obtained from the animal, in situ hybridization analysis, Western analysis, immunoassays such as enzyme-linked immunosorbent assays and reverse-transcriptase PCR (RT-PCR). A Tau pathology can be manifested as, for example, neurofibrillary tangles or neuronal and/or glial inclusions or insoluble deposits that stain positively with anti-Tau antibodies. Anti-Tau antibodies are available commercially from, for example, Sigma Chemical Company (St. Louis, Mo.). Anti-Tau antibodies that are sensitive to phosphorylated epitopes of Tau are available from Innogenetics (Belgium).

As described herein, expression of human tau containing a P301L mutation results in motor and behavioral deficits in transgenic mice, with age- and gene dose-dependent development of neurofibrillary tangles (NFT). This phenotype occurred as early as 6.5 months in hemizygous and 4.5 months in homozygous animals. In addition, the phenotype was observed in transgenic mice expressing a mutant Tau polypeptide with N-terminal inserts and in transgenic mice expressing a mutant Tau polypeptide without an N-terminal insert. NFT and Pick-body-like neuronal lesions occurred in the amygdala, septal nuclei, pre-optic nuclei, hypothalamus, midbrain, pons, medulla, deep cerebellar nuclei and spinal cord, with tau-immunoreactive pre-tangles in the cortex, hippocampus and basal ganglia. Areas with the most NFT had reactive gliosis. Spinal cord had axonal spheroids, anterior horn cell loss, and axonal degeneration in anterior spinal roots. Peripheral neuropathy and skeletal muscle with neurogenic atrophy also resulted. Brain and spinal cord contained insoluble tau that co-migrated with insoluble tau from AD and FTDP-17 brains. The phenotype of mice expressing P301L mutant tau mimics features of human tauopathies, especially progressive supranuclear palsy.

In one embodiment, the transgenic non-human mammals further include a nucleic acid construct encoding human presenilin-1 (PS-1) protein or a human amyloid precursor protein (APP). The nucleic acid sequence encoding human PS-1 protein has GenBank Accession Nos. L76518–L76528. The nucleic acid sequence of human APP has GenBank Accession No. D87675 g2429080. Alternative splicing of the human APP gene produces three APP isoforms, APP751, APP770, and APP695. Mutant APP polypeptides are particularly useful and are numbered herein according to the APP770 isoform. For example, the human APP can have a mutation at amino acid 692 in which alanine is replaced with a glycine, a mutation at amino acid 717 such as the substitution of a phenylalanine or glycine residue for valine, or a mutation at amino acids 670 and 671 in which asparagine and leucine residues replace lysine and methionine residues (K670N-M671 L). The K670N-M671 L mutation is referred to as the Swedish mutation. See, Mullan et al., *Nature Gen.*, 1:345–347 (1992) and U.S. Pat. No. 5,455,169.

Expression of APP (e.g., APP containing a mutation such as the Swedish mutation) or PS-1 and a mutant tau polypeptide can enhance the Tau pathology in the transgenic non-human mammal as compared with control transgenic non-human mammals expressing only a mutant tau polypeptide. "Control" typically refers to the same background strain and same species of transgenic non-human mammal, e.g., both non-human mammals are rats or both are mice. As described herein, transgenic mice expressing a mutant tau and a mutant APP polypeptide develop both Aβ plaques and an enhanced tau pathology, including granulovacuolar degeneration, an increased number of NFTs, and an increased amount of insoluble tau. Although neither elevated APP/Aβ nor extensive Aβ deposition is necessary for tangle formation, elevated APP/Aβ enhanced the pathological nature of a mutant tau polypeptide (P301L). The phenotype of the mutant tau/mutant APP mice indicates that APP/Aβ and tau directly interact. Such mice represent an important Alzheimer's disease model that can be used to screen for therapies that address the amyloid deposition, tangle accumulation, and neuronal loss that occurs in Alzheimer's disease and related disorders.

Transgenic non-human mammals expressing a Tau polypeptide and APP or PS-1 can be produced by crossing transgenic non-human mammals overexpressing human three-repeat or four-repeat tau cDNAs (wild type cDNAs or cDNAs containing pathogenic mutations) with transgenic non-human mammals overexpressing human APP and/or human PS-1 cDNAs. Transgenic mice overexpressing human APP or human PS-1 are described, for example, in WO 97/48792 and WO 97/27296, respectively. See, U.S. Pat. No. 5,877,399 for a description of transgenic mice containing human APP with the Swedish mutation and WO 98/17782 for a description of transgenic mice containing mutant APP and mutant PS-1 transgenes. Alternatively, a single line of transgenic non-human mammals can be produced by initially preparing the non-human mammals using the appropriate constructs.

The ratio of Tau polypeptide containing four microtubule binding motifs to Tau polypeptide containing three microtubule binding motifs (i.e, ratio of four-repeat to three-repeat isoform) plays a role in the correct functioning of the Tau protein. As described herein, the splicing mutations affect the relative levels of four-repeat Tau and three-repeat Tau proteins, which may have important implications for the modeling of Alzheimer's disease since mouse brains contain nearly all four-repeat Tau (almost the direct opposite of the human brain). The mouse tau gene lacks a "stable" stem-loop structure to regulate alternate splicing of exon 10 leading to the presence of a single isoform. Prior to the animal models described herein, transgenic mouse models of Alzheimer's disease expressed APP at high levels, developed amyloid plaques (Aβ plaques) and contained hyperphosphorylated Tau polypeptide, but did not contain Tau positive tangles or exhibit significant cell loss.

Therefore, it appears that there is a difference in the response of mouse and human neurons to an amyloid insult. Given the evidence of Tau involvement in neurodegeneration, provided by the mutations described herein, and the dramatic difference in the ratio of four-repeat and three-repeat Tau isoforms in the mouse and human brains, Tau polypeptide seems a likely candidate to explain the difference in the response of mouse and human neurons to amyloid. This hypothesis is further strengthened by the observation, again from the splice site mutations described herein, that the ratio of four-repeat to three-repeat Tau is indeed important to Tau function. Disturbances in this ratio can lead to neurodegeneration. The fact that mice have a preponderance of four-repeat Tau isoform also may be significant since four-repeat Tau protein binds more tightly to microtubules (compared to three-repeat Tau) and produces more stable microtubules. It is possible therefore that the mouse is better able to withstand the process induced by amyloid (Aβ) that leads to neurodegeneration and Alzheimer's disease in humans. As described herein, however, transgenic mice expressing mutant APP and mutant four-repeat Tau develop both NFTs and amyloid plaques.

The transgenic non-human mammals described herein can be used to screen for agents that inhibit the development of Tau pathologies or agents that can be used for the treatment of disorders associated with Tau pathologies. Different aged transgenic non-human mammals can be used, depending on whether the end point is inhibiting the development of the pathology or treatment of a disorder. For example, a test agent can be administered to a transgenic non-human mammal of the invention prior to development of Tau pathology, then development of a Tau pathology is monitored and compared with that of a corresponding transgenic non-human mammal to which the test agent has not been administered. In embodiments in which agents are being screened for treatment of a disorder associated with a Tau pathology, the agents are administered to transgenic non-human mammals that have developed the Tau pathology, then the Tau pathology or symptoms of the disorder are monitored in the transgenic non-human mammal and compared with that of transgenic non-human mammals to which the test agent has not been administered.

Methods for Diagnosing Neurodegenerative Diseases

In another aspect, the invention features a method for determining a diagnosis, prognosis, or risk of neurodegenerative disease in a patient. The method includes detecting a tau gene mutation in genomic DNA of the patient, wherein the mutation is linked to a Tau pathology. Neurodegenerative diseases, include, for example, FTDP-17, Pick's disease, Progressive Supranuclear Palsy (PSP), Corticobasal degeneration (CBD), lytico and bodig disease of Guam, variants of AD with straight tau filaments, and any other neurodegenerative diseases in which Tau pathology is a major feature. Tau pathology includes neurofibrillary tangles observed in brain, including one or more of the following: paired helical filaments (PHFs), straight Tau filaments and any other type of Tau filament. Tau pathology also includes neuronal and/or glial inclusions or insoluble deposits that stain positively with anti-Tau antibodies.

Tau gene mutations can be detected by various methods. Mutations can be detected, for example, by sequencing exons and introns of the tau gene, restriction fragment length polymorphisms (RFLP) analysis, PCR-RFLP analysis, allele-specific hybridizations, mutation specific polymerase chain reactions (MSPCR), or by single stranded conformational polymorphism (SSCP) detection.

Genomic DNA is generally used in the detection of tau gene mutations. Genomic DNA typically is extracted from peripheral blood samples, but also can be extracted from, for example, mucosal scrapings of the lining of the mouth. Brain tissue obtained from an autopsy also can be used for post-mortem diagnosis. Routine methods can be used to extract genomic DNA from a blood or tissue sample, including, for example, phenol extraction. Alternatively, genomic DNA can be extracted with kits such as the QIAamp® Tissue Kit (Qiagen, Chatsworth, Calif.), Wizard® Genomic DNA purification kit (Promega, Madison, Wis.), and the A.S.A.P.™ Genomic DNA isolation kit (Boehringer Mannheim, Indianapolis, Ind.).

For example, exons and introns of the tau gene can be amplified through PCR and then directly sequenced. This method can be varied, including using dye primer sequencing to increase the accuracy of detecting heterozygous samples. Alternatively, a nucleic acid molecule can be selectively hybridized to the PCR product to detect a gene variant. Hybridization conditions are selected such that the nucleic acid molecule can specifically bind the sequence of interest, e.g., the mutant nucleic acid sequence. Such hybridizations typically are performed under high stringency as many mutations include only a single nucleotide difference. High stringency conditions can include the use of low ionic strength solutions and high temperatures for washing, for example, 0.015 M NaCl/0.0015 M sodium citrate (0.1X SSC), 0.1% sodium dodecyl sulfate (SDS) at 60° C. Alternatively, denaturing agents such as formamide can be employed during hybridization, e.g., 50% formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is the use of 50% formamide, 5X SSC (0.75 M NaCl, 0.075 M sodium citrate), 50 mM sodium phosphate (pH 6.8), 0.1% sodium pyrophosphate, 5X Denhardt's solution, sonicated salmon sperm DNA (50 $\mu$g/ml), 0.1% SDS, and 10% dextran sulfate at 42° C., with washes at 42° C. in 0.2X SSC and 0.1% SDS. Hybridization conditions can be adjusted to account for unique features of the nucleic acid molecule, including length and sequence composition.

PCR-RFLP analysis can be performed in the following manner. If a tau mutation introduces a restriction site, restriction digest with the particular restriction enzyme can differentiate wild-type tau from mutated tau. For example, missense mutation of a proline to leucine at amino acid 301 can be detected by BstNI or SmaI digestion of exon 10 PCR products. The mutant allele contains a BstNI site, whereas the normal allele contains a SmaI site. The exon 10 splice donor +16 mutation can be detected by NspI digestion. Again, the mutant allele is cleaved while the normal allele is not cleaved by NspI. The exon 10 splice donor +13 and +14 mutations eliminate an AflIII site from the amplification product. For tau mutations that do not alter a common restriction site, primers can be designed that introduce a restriction site when the mutation is present, or when the wild-type sequence is present.

PCR conditions and primers can be developed that amplify a product only when the mutation is present or only when the wild-type tau is present (MSPCR or allele-specific PCR). For example, patient DNA and a control can be amplified separately using either a wild-type primer or a primer specific for the mutation. Each set of reactions then is examined for the presence of amplification products using standard methods to visualize the DNA. For example, the reactions can be electrophoresed through an agarose gel and DNA visualized by staining with ethidium bromide or other DNA intercalating dye. In DNA samples from heterozygous patients, reaction products would be detected in each reaction. Patient samples containing solely wild-type tau would have amplification products only in the reaction using the wild-type primer. Similarly, patient samples containing solely mutated tau would have amplification products only in the reaction using the variant primer.

Mismatch cleavage methods also can be used to detect differing sequences by PCR amplification, followed by hybridization with the wild-type sequence and cleavage at points of mismatch. Chemical reagents, such as carbodiimide or hydroxylamine and osmium tetroxide can be used to modify mismatched nucleotides to facilitate cleavage.

Alternatively, the ratio of exon 10+ and exon 10− RNA can be measured and used for determining a diagnosis, prognosis or risk of neurodegenerative disease in a patient. For example, reverse transcriptase PCR (RT-PCR) can be performed on total RNA isolated from a patient. After amplification, PCR products can be resolved into fragments with and without exon 10, and the molar ratio of exon 10+ to exon 10− RNA can be determined using densitometry. Patients with an increase in the proportion of exon 10+ RNA can have a mutation in the splice donor sites of the tau gene.

The invention will be further described in the following examples, which do not limit the scope of the invention described in the claims.

EXAMPLES

Example 1

General Methods:

Tau gene sequencing Tau exons were PCR amplified from genomic DNA from family members with primers designed to flanking intronic sequence. Each reaction contained approximately 0.8 pM of each primer and 1 unit of Taq "Gold" polymerase (Perkin Elmer). Amplification was performed using a 60° C. to 50° C. touchdown protocol over 35 cycles, with a final extension of 72° C. for 10 min. PCR products were purified using a Qiagen PCR kit and their concentration estimated on an agarose gel. DNA (100 ng) for each exon was sequenced on both strands using the dRhodamine dye terminator cycle sequencing kit (Perkin Elmer) and relevant PCR primers. Sequencing was performed on an ABI377 automated sequencer. Heterozygote base calls were made using Factura software (Perkin Elmer) and sequence alignment was performed by Sequence Navigator (Perkin Elmer).

Mutation detection Mutations were detected in families (for segregation analysis) and controls using sequencing as described above, or PCR-RFLP analysis. Missense mutation P301L was detected by BstNI or SmaI digestion of exon 10 PCR products. The mutant allele contained a BstNI site, whereas the normal allele contained a SmaI site. The exon 10 splice donor +16 mutation was detected by NspI digestion, in which the mutant allele was cleaved by NspI. In contrast, the exon 10 splice donor +13 and +14 mutations eliminated an AflIII site from the amplification product. After digestion, genotyping was performed using 3% Metaphor (FMC) agarose gels.

RT-PCR analysis of exon 10 alternative splicing Total RNA was prepared from a section of frontal lobe from seven normal brains and from the frontal lobes of four FTDP-17 brains using the Trizol reagent and protocol (Life Technologies). Two of the FTDP-17 brains were from families with splice donor site mutations (DDPAC and Aus1) and two were from family FTD003 with the P301L point mutation. Reverse transcription was performed using the Superscript preamplification kit (Life Technologies) on 1–4 µg of brain RNA with an oligo dT primer. PCR was performed between exon 9 (Forward 5'-ATCGCAGCGGCTACAGCAG-3', SEQ ID NO:1) and exon 11 (Reverse 5'-TGGTTTATGATGGATGTTGCC-3', SEQ ID NO:2) and between exon 9 and exon 13 (Reverse 5'-TCTTGGCTTTGGCGTTCTC-3', SEQ ID NO:3). Preliminary PCR reactions were performed using a range of amplification ncycles to determine the optimum number of cycles for this analysis. Based on the results of this initial study, 32 cycles were used in subsequent experiments. After amplification, PCR products were electrophoresed through a 2% Metaphor agarose gel where they resolved into two major fragments (327 and 418 bp, exon 9–11, 487 bp and 578 bp, exon 9–13) corresponding to tau transcripts with and without exon 10. The molar ratio of exon 10+ to exon 10– RNA was determined using a Kodak DC120 camera kit and ID Image Gel densitometry software. Three independent PCR reactions (for both Ex9–11 and Ex9–13) were used to determine the mean ratio for each brain. After ratios were determined for all experiments, a comparison of FTDP-17 mutant splice site brains was made against normal and FTDP-17 brains with the P301L point mutation using single tailed t-tests.

Exon-trapping analysis of exon-10 splicing Mutant and wild-type versions of tau exon 10 were amplified from the DNA of patients with each of the three different splice mutations (+13, +14, and +16) and from normal individuals. PCR products contained exon 10 and approximately 40 bp of flanking intron sequence at either end. PCR products were cloned into the splicing vector pSPL3b using XhoI and PstI sites incorporated into the amplification products. Mutant and wild-type constructs were identified by sequence analysis. For exon trapping, the exon-trapping system of Life-Technologies was used. Briefly, COS-7 cells were transfected in duplicate with 1 µg of each construct using LipofectACE reagent (Life Technologies). Cells were collected 24 h post-transfection and RNA prepared using the Trizol reagent (Life Technologies). First-strand synthesis and nested PCR were done using reagents supplied with the system and conditions described in manufacturer's instructions, except that BstXI digestion of primary PCR products was excluded. To verify that RT-PCR was quantitative, different amounts of primary PCR template (1 to 5 µl) were used and the total number of amplification cycles was varied (30–35 cycles). PCR products were analyzed on 3% Metaphor (FMC) gels. Identity of RT-PCR products was confirmed by sequencing.

Example 2

Detection of Pathogenic Mutations in Tau: A missense mutation was detected in exon 10 in two families (Table 2); a large Dutch kindred, Hereditary Frontal Temporal Dementia I (HFTDI) that had previously been linked to chromosome 17, and a small U.S. kindred (FTD003). This mutation results in the substitution of proline to leucine at codon 301 (P301L), numbered from the longest isoform (FIG. 1C).

TABLE 2

Families with segregating mutations within the tau gene

| Family ID | Origin (founder) | Affected (PM confirmed) | Generations | Mean onset age (years) | Mutation |
|---|---|---|---|---|---|
| HFTD2* | Netherlands | 34(15) | 7 | 47 | G272V |
| HFTD1* | Netherlands | 49(14) | 5 | 50 | P301L |
| FTD003 | USA | 3(2) | 2 | 45–50 | P301L |
| Man19 | UK | 3(1) | 2 | 65 | Ex 10 splice + 13 |
| DDPAC* | Ireland | 13(6) | 3 | 44 | Ex 10 splice + 14 |
| AusI* | Australia (UK) | 28(5) | 5 | 53 | Ex 10 splice + 16 |
| FTD002* | USA | 3(1) | 2 | 40 | Ex 10 splice + 16 |
| Man6 | UK | 2(1) | 1 | 48 | Ex 10 splice + 16 |
| Man23* | UK | 10(2) | 3 | 51 | Ex 10 splice + 16 |
| FTD004 | USA | 10(2) | 4 | 55 | R406W |
| HFTD4 | Netherlands | 2 | 2 | 53 (one patient) | Deletion of K280 |

*Families that displayed prior evidence of genetic linkage to chromosome 17.

A G272V mutation was found in a second large Dutch kindred HFTD2 (Table 2) that had originally been described as having hereditary Pick's disease indicating the considerable clinical overlap between Pick's disease and FTDP-17. The G272V mutation also affects a highly conserved residue within a microtubule binding domain encoded by exon 9, and again, this mutation affects the specific region that interacts with the microtubule. Indeed, within the imperfect repeat sequence that makes up the four microtubule binding domains, the G272V and P301L mutations affect the residue equivalent to G303, that are separated by only one residue. Thus, for P301L, the PGGG motif in the binding repeat becomes LGGG, and for G272V, the motif becomes PGVG. In contrast to the P301L mutation (exon 10), the G272V mutation (exon 9) will affect all Tau isoforms. The G272V and P301L mutations were found to segregate with disease in each of the relevant families. Both mutations were absent from 192 Dutch controls and the P301L mutation also was absent from a further 150 Caucasian control individuals from a Florida patient series. Thus, these data taken together indicate that the G272V and the P301L mutations that likely affect Tau microtubule binding are pathogenic in HFTD2 (G272V) and in HFTDI and FTD003 (P301L).

A third tau missense mutation (R406W) was detected in exon 13, in a single family from the USA (FTD004). It alters a highly conserved residue near the C-terminus. The R406W mutation segregates with the disease in this family and was absent from 150 controls collected in the USA. The distribution of Tau positive inclusions in FTD004 meets NINDS neuropathologic criteria for PSP. Electron microscopy revealed, however, that the Tau filaments in this family are AD-like PHFs and not the straight Tau filaments normally observed in PSP. The clinical phenotype includes memory loss and personality change and would be unusual for PSP. The neuropathological phenotype in this family also is highly similar to that of the lytico and bodig diseases of Guam. The pathogenic mechanism of R406W remains unclear. The proximity of this mutation to key residues that are phosphorylated in PHF Tau (Ser396, Ser404), however, suggests that this mutation may in some way influence Tau phosphorylation and thus the formation of PHFs.

In addition to the missense mutations, three heterozygous mutations were observed in a cluster of 4 nucleotides 13–16 bp 3' of the exon 10 splice donor site (FIG. 2). Six families (Table 2) had mutations at these three sites including four families which had previously displayed evidence for linkage to chromosome 17 (DDPAC, Aus1, FTD002, and Man23). In each of the six families, the relevant mutation was found to segregate with disease (FIG. 1a). None of the 3 intronic mutations were observed in 150 USA and 23 UK caucasian control individuals. These data, together with the presence of the mutations in such a tight cluster in close proximity to the exon 10 splice donor site and the number of affected FTD families (6), indicates that these variants were pathogenic.

Example 3

Figure 2C:
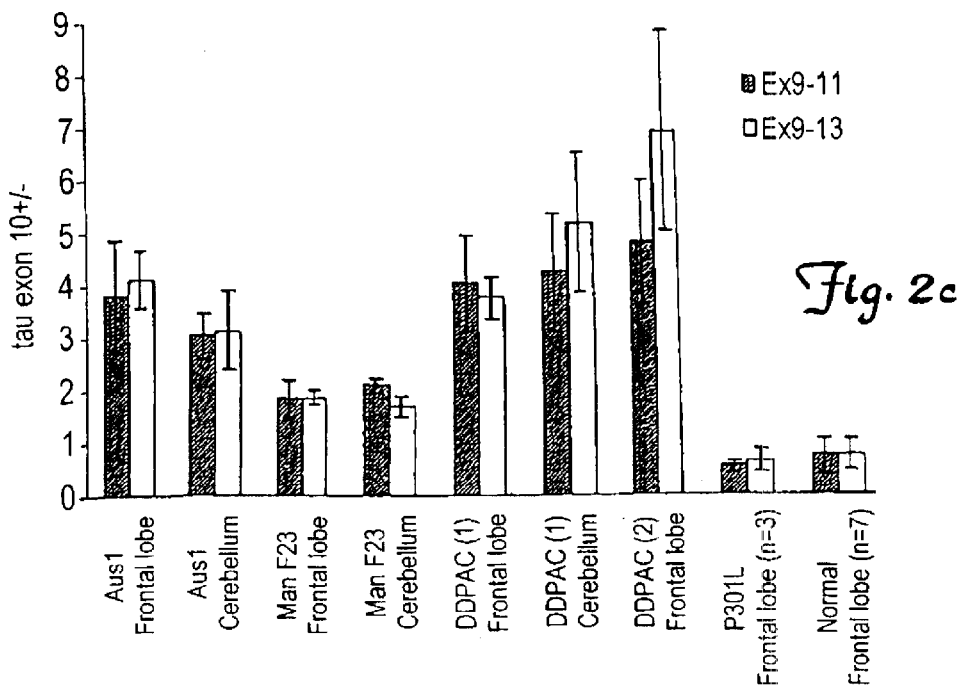
FIG. 2C is a graph representing the RT-PCR analysis of the molar ratio between tau mRNA + and − exon 10 in different brains. Amplification results from exons 9–11 are shown as white bars and from exons 9–13 as hatched bars.

Ratio of Tau Exon $10^+$ RNA to Exon $10^-$ RNA in Patients: RT-PCR was used to estimate the ratio of tau exon 10+ RNA to exon 10– RNA in four FTDP-17 brains. Two of the brains were from families with splice donor site mutations, DDPAC and AusI, and two were from the FTD003 family with the P301L mutation. RT-PCR was performed to amplify a product between exon 9 and exon 11 and, in a separate reaction, between exon 9 and exon 13. Both these amplifications generate two products, one corresponding to tau transcripts containing exon 10 and one corresponding to tau transcripts in which exon 10 is skipped. In both PCRs, the brains containing the splice mutations (DDPAC and Aus1) gave a 2–4 fold higher proportion of tau exon 10 + RNA as compared with 7 control brains (FIG. 2C). RNA from frontal lobe (4 cases) and cerebellum (3 cases) from FTDP-17 brains with splice site mutations (DDPAC (2 brains), ManF23 and AusI) have molar ratios >1.6 (left 14 bars of FIG. 2C). RNA from the frontal lobes of normal brains (n=7) and three FTDP-17 brains with the P301L mutations have ratios <0.8 (right 4 bars of FIG. 2C). The FTDP-17 brains in which splice mutations were not identified gave similar ratios to that of the controls (FIG. 2C), indicating that the increase in the ratio in the splice site mutation brains was not simply an inevitable consequence of the disease process. The increase in the proportion of exon 10+ tau RNA (2–4 fold) is most consistent with the complete or virtually complete elimination of exon 10– tau mRNA generated from the mutant allele.

Example 4

Impact of 5' Splice Site Mutations on Alternative Splicing: Exon-trapping assays were used to test the effect of the 5' splice site mutations on alternative splicing of tau exon 10. Wild-type and three mutant versions (+13, +14, and +16) versions of exon 10 were analyzed. These nucleic acid molecules, which included approximately 40 bp of intronic sequence at either end, were amplified, and cloned into the splicing vector pSPL3b, which contains exons from the rabbit β-globin and HIV tat genes. A multiple cloning site in an intron between the two tat exons allows test DNA to be introduced. An SV40 promoter in pSPL3b drives the generation of artificial mRNAs when the construct is transfected into COS7 cells, trapping any functional exons in the cloned DNA between the two tat exons, so they can be detected by RT-PCR. Data from all constructs were derived from two independent transfections. The identity of all RT-PCR products was verified by sequence analysis.

PCR products result from splicing of pSPL3b vector-derived tat exons with (270 bp) and without (177 bp) tau exon 10 (FIG. 3A). The sizes of minor products 299 bp and 206 bp in length correspond to exon 10+ and exon 10– transcripts, respectively, into which 29 bp of additional vector sequence was incorporated into the 5' tat exon, are shown in brackets. This artifact does not affect the splicing of exon 10 between the two tat exons. The position of nested RT-PCR primers is indicated by arrows.

Figure 3B:
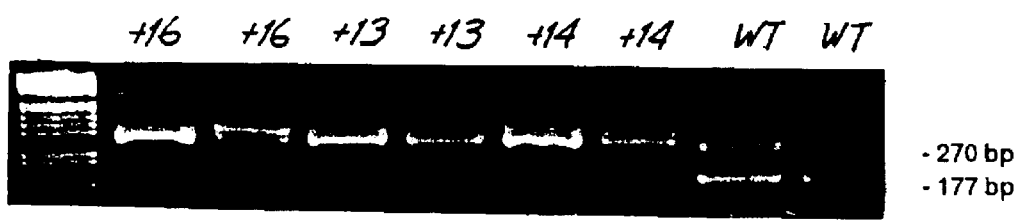

Wild-type constructs gave strongest signals from bands (177 bp, 206 bp) corresponding to exon 10– vector-only splicing, with the most prominent being at 177 bp (exon 10– RNA) (FIG. 3B). Weaker products at 270 bp corresponded to exon 10+ transcripts. With the mutant constructs, tat to tat spliced vector-only transcripts (177 bp) were greatly reduced, consistent with increased usage of the exon-10 5' splice site. 5' splice site mutants (+16, +13, and +14) gave strongest signals corresponding to exon 10+ transcripts (270 bp, 299 bp), with products corresponding to exon 10– vector-only splicing (177 bp, 206 bp) dramatically reduced and virtually absent in +13 and +14. These results show that the 5'-splice-site mutants increase splicing of exon 10 in vitro. The data suggest that the splice donor site mutations observed in 6 FTDP-17 families act by increasing the proportion of tau mRNA that contains exon 10 and which encodes the four-repeat Tau protein isoform.

Example 5

Production and Analysis of Transgenic non-human mammals: To examine the effects of the P301L mutation, human P301L or wild-type (WT) tau cDNAs containing exons 2, 3, and 10 ($2^+3^+10^+$), or containing exon 10 and lacking exons 2 and 3 ($2^-3^-10^+$) were expressed under control of the mouse prion promoter (MoPrP). These cDNAs encode either four-repeat tau without N-terminal inserts (4R0N, exons $2^-3^-10^+$) or four-repeat tau with 2 N-terminal inserts (4R2N, exons $2^+3^+10^+$). See Trjanowski and Lee, Brain Pathol., 9:733–739 (1999) for tau isoform nomenclature. Mice normally have 4R0N, 4R1N, and 4R2N tau isoforms. Tau cDNAs (exons 1, 4–5, 7, 9–13, intron 13, and exon 14) were provided by Dr. Athena Andreadis. Mutagenesis was performed using a Promega Gene Editor site-directed mutagenesis kit and following the manufacturer's recommendations, using P301L (5'P-dAACACGTCCTGGGAGGCG3', SEQ ID NO: 10) and selection (5'P-dCCGCGAGACCCACCCTTGGA GGCTCCAGATTTATC3', SEQ ID NO: 11) primers, and confirmed by sequencing with the BigDye Terminator Sequencing Kit (Perkin Elmer) on an ABI377 automated sequencer with Sequence Navigator software (Perkin Elmer).

Transgenic constructs were generated by ligating a SalI fragment of each tau construct into a XhoI linearized mouse prion promoter (MoPrP) vector. See, Borchelt et al., Genet. Anal., 13:159–163 (1996) for a description of the MoPrP vector. Constructs were linearized with NotI, gel purified, and digested with β-agarase under manufacturer's conditions (New England Biolabs). DNA was filtered, concentrated, and diluted to 3 ng/μl for wild-type, four repeat tau (WT4R) or 7 ng/µl for the DNA encoding the P301L mutation in microinjection buffer (5 mM Tris-HCl pH 7.4, 10 mM NaCl, 0.1 mM EDTA).

Transgenes were microinjected into fertilized mouse (C57BL/DBA2/SW) eggs and reimplanted into pseudopregnant female according to standard procedures. Founders were screened by PCR between exons 1 and 5 of the human tau cDNA against an internal pre-senilin-2 control PCR.

In Situ hybridization—Frozen mouse brains were sectioned at 15 µM. Human specific synthetic oligomers to exon 1 (5'CTTTCAGGCCAGCGTCCGTGTCACCCTCTT GGTC3', SEQ ID NO:12) and exon 5 (5'TTT GTCATCGCTTCCAGTCCCGTCTTTGCTTTTAC3', SEQ ID NO: 13) of human tau cDNA were 3'-end labeled with α[$^{35}$S]dATP (NEN DuPont). Slides were fixed, dehydrated, and hybridized overnight at 37° C. with labeled oligonucleotide. Control sections were hybridized in the presence of a 50-fold molar excess of unlabeled oligonucleotide. After hybridization, slides were stringently washed, dehydrated, and exposed to Hyperfilm β-Max (Amersham) for 1–2 weeks.

Western Analysis—Insoluble tau extraction and dephosphorylation were performed as previously described on frozen brains. See Greenberg and Davies, *Proc. Natl. Acad. Sci. USA*, 87:5827–5831 (1990); and Greenberg et al., *J. Biol. Chem.*, 267:564–569 (1992). Soluble and insoluble tau were electrophoresed through 7.5% SDS/PAGE gels, transferred to nitrocellulose and stained with a human tau-specific polyclonal antibody (E1, aa# 19–33) and with antibodies (WKS45, Tau46) that recognize both human and mouse tau. Antibodies AT100 and AT180 that recognize tau phosphoepitopes were also used. Brains and spinal cords were prepared in the same volume; therefore, the amount of insoluble tau loaded from the spinal cord was 4–5 fold less than that loaded from the brains.

Tau ELISAs—Mouse hemibrains were homogenized at a w/v ratio of 100 mg/ml, in TBS containing protease and phosphatase inhibitors, serially diluted and used to coat Maxi-sorb ELISA plates. Samples were evaporated to dryness at 37° C. and blocked in TBS containing 5% non-fat, dry milk. Anti-tau monoclonals, human tau (CP27) and total tau (MN37 and Tg5), were added to the ELISA plates at 1:20 dilutions. Following incubation at 4° C. overnight, plates were washed in TBS containing 0.5% Tween 20 and incubated with goat anti-mouse antibodies coupled to horseradish peroxidase (HRP). Plates were washed and bound antibodies were quantified using ABTS peroxidase substrate (Biorad). The ratio of human tau to total tau was assessed.

Immunohistochemistry—Perfused (0.9% saline followed by 4% paraformaldehyde) or immersion fixed (4% paraformaldehyde) brain sections were immunostained with the following tau antibodies: MC-1 (Davies, 1:25–1:50), AT8 (1:5000) and AT180 (1:100) (Endogen); CP3 (Davies; 1:100); CP9 (Davies; 1:100); CP 13 (Davies; 1:100), PHF-1 (Davies; 1:100), Alz50 (Davies, 1:10), E-1 (Yen; 1:1000) and α-B crystallin (Novacastra; 1:1000); ubiquitin: UH19 (Ksiezak-Reding; 1:500); NFT antibody: Ab39 (Yen; 1:20); Ab69 (Yen; 1:20); TG3 (1:10); GFAP (Biogenex, 1:100); and phosphorylated neurofilament (Sternberger-Meyer; SMI-31; 1:5000) using standard avidin or streptavidin biotin peroxidase methods. Double immunostaining was performed on free floating vibratome sections of brainstem incubated with rabbit GFAP and CP13 or Alz50 and SMI-31, followed 16 hours later with isotype specific second antibodies conjugated to fluorescein or rhodamine. MC-1 recognizes a unique conformation of human tau similar to that seen in AD brains. See, Jicha et al., *J. Neurosci. Res.*, 48:128–132 (1997). Paraffin embedded sections were used for histochemical stains (hematoxylin & eosin), thioflavin-S, Congo red, and silver stains.

Electron microscopy (EM)—The brain stem, spinal cord and skeletal muscle from perfused mice (4% paraformaldehyde) were dissected and immersion fixed in paraformaldehyde. For pre-embedding, immuno-EM was performed as described above. The immunolabeled areas were dissected, fixed in $OsO_4$, dehydrated and embedded in Epon. For post-embedding immuno-EM, small pieces of fixed tissue from brainstem and spinal cord were embedded in LR White resin. Primary tau antibodies (CP13) were used to stain ultrathin sections on nickel grids, followed by gold-conjugated secondary antibodies. For routine ultrastructural studies, mice were perfused with 2% glutaraldehyde/2% paraformaldehyde/0.1 M cacodylate buffer, pH 7.4, and the tissues were immersion fixed in the same fixative for another 4 hr, followed by $OsO_4$ and uranyl acetate, then dehydrated and embedded in Epon.

Neuronal Cell Counts—Cell counts were performed on matching lumbrosacral and cervical enlargement 5 µM paraffin sections of P301L (JNPL3) and non-transgenic mice stained with H&E. Neuronal counts were from every fifth section from images captured by CCD camera. 30 sections were counted from each animal.

Example 6

Tau Pathologies of Transgenic Non-Human Mammals: Based on ELISA, Western and Northern analyses, a P301L founder line (JNPL3, 4R0N) and two WT4R lines (JN4 and JN25) with the highest transgene expression were expanded. The tau transgene expressed at approximately endogenous tau levels in JNPL3 and JN25 mice (~50% of total tau) and below endogenous levels in JN4 mice (~25% of total tau). Homozygous JNPL3 mice expressed human P301L tau at approximately two-fold hemizygous levels. A largely neuronal transgene expression pattern was demonstrated by in situ hybridization, with strongest signals in the cerebellum and hippocampus followed by the thalamus, hypothalamus, spinal cord, brain stem and cortex.

The absence of escape extension during tail elevation and spontaneous back paw clenching while standing was detected in F1 JNPL3 hemizygotes as early as 6.5 months (21 animals) and in F2 JNPL3 homozygotes at 4.5 months (4 animals). By 10 months, ~90% of JNPL3 mice developed motor and behavioral disturbances. JNPL3 mice showed delayed righting response and eventually became unable to right. In hang tests, JNPL3 mice fell after grasping the rope briefly, whereas JN4, JN25 and non-transgenic mice held with three limbs and tail without falling. Within two weeks of phenotype onset, JNPL3 animals could not ambulate. Weakness spread to all limbs and dystonic posturing developed. Reduction in weight, grooming, vocalization, and increased docility occurred in affected animals. JNPL3 mice (19 of 21 examined) developed eye irritations with difficulty opening their eyes. Within 3–4 weeks of initial signs, mice became moribund. JN4, JN25, and non-transgenic animals appeared normal.

JNPL3 mice with motor and behavioral disturbances were examined for neuropathological changes. Spinal cords of affected P301L mice showed fibrillary gliosis in the anterior horns, axonal degeneration in the anterior roots, and axonal spheroids. Motor neuron counts of P301L mice showed ~48% reduction in the spinal cord. Gliosis (GFAP immunoreactivity) also occurred in the brainstem, diencephalon and basal telencephalon. NFT were identified in the diencephalon, brainstem, cerebellar nuclei and spinal cord by tau immunostaining that were confirmed by Congo red, thioflavin-S fluorescent microscopy, Gallyas (See Labal et al. *Neurobiol. Aging,* 12:357–361 (1991)), Bielschowsky, and Bodian silver stains. Apparent extracellular tangles in the spinal cord were consistent with motor neuron loss. Granular somatodendritic tau immunoreactivity consistent with "pre-tangles" and tau-positive processes occurred with a wider distribution in the brain than NFT, including neurons in the cortex (especially piriform and entorhinal cortices), hippocampus and basal ganglia.

Tau-positive NFT appeared morphologically heterogeneous, including flame- or globose shaped NFT, as well as Pick bodies and smaller more irregular dense cytoplasmic inclusions similar to those found in FTDP-17 and CBD. See Dickson, *Ann. Neurol.,* 42:541–544 (1997); and Mira et al., *J. Neuropath. Exp. Neurol.,* 58:335–345 (1999). Neuronal lesions were immunoreactive with tau antibodies recognizing conformational (Ab39, Ab69, Alz50, MC1), phosphorylated (AT8, AT180, CP3, CP9, CP13, PG5, PHF-1, TG3) and nonphosphorylated (E1) epitopes, and were intensely immunoreactive for ubiquitin (UH19). NFT were not immunoreactive for α-B crystallin or phosphorylated neurofilament (SMI-31).

Ultrastructurally, brainstem and spinal cord neurons with NFT had filamentous aggregates in the perikarya and proximal dendrites. Filaments were randomly oriented, were not membrane-bound, and were immunoreactive for phosphorylated and nonphosphorylated tau. Most filaments were straight (10 to 30 nm diameter); others had a twisted ribbon appearance. Affected neurons also showed chromatin dispersal, nuclear membrane infolding, Nissl body reduction, and increased polysomes. Reactive astrocytes with abundant glial filaments, but not tau inclusions, occurred in the vicinity of NFT.

Skeletal muscle showed groups of small acutely angulated fibers consistent with neurogenic atrophy. Ultrastructurally, the atrophic fibers had disorganized sarcomeres, increased glycogen and lipofuscin and redundant basement membranes, but myopathic changes were absent. Peripheral nerves had extensive axonal degeneration with segmental swelling of axon fibers and advanced myelin degeneration.

Non-transgenic littermates, JN4, or JN25 mice up to 10 months of age lacked these pathological changes; however, MC-1 positive cell bodies were identified in the cortex, hippocampal pyramidal layer, hippocampal dentate gyrus and cerebellar dentate nucleus in the highest expressing WT4R line (JN25).

The spinal cord pathology observed in the JNPL3 mice correlated with motor dysfunction. The appendicular weakness is consistent with anterior horn cell loss and degeneration and skeletal muscle denervation atrophy. The severe neurofibrillary pathology in the basal forebrain and the reticular system throughout the brainstem of P301L mice is consistent with the docility observed. The marked hypothalamic involvement may contribute to the cachexia of end-stage animals. Finally, degeneration of cranial nerve nuclei including the motor nucleus of the trigeminal nerve and hypoglossal nucleus could explain the lack of vocalization in P301L animals.

Tau filament aggregation in JNPL3 mice accompanied decreased tau solubility. Sarkosyl insoluble tau from brains and spinal cords of JNPL3 mice at progressive ages, littermate controls, JN4 and JN25 (WT4R) mice was examined by Western blot using human tau-specific antibody (E1). Human tau with normal mobility was present in soluble fractions only in transgenic mice. Only the JNPL3 (P301L) mice had sarkosyl insoluble tau. A prominent insoluble tau band migrating slower (~64 kD) than the normal expressed human 4R0N tau was observed along with a diffuse protein smear at the top of the gel, consistent with aggregated tau. Higher molecular weight insoluble tau species increased and soluble human tau decreased with age suggesting a shift of tau to the insoluble pool as NFT form. Comparison of insoluble tau from JNPL3 mice with that from human FTDP-17 (P301L) and AD brains revealed marked similarities including co-migration of a prominent 64 kD band. Dephosphorylation of the sarkosyl-insoluble tau eliminated the slower migrating tau bands, including the 64 kD band, demonstrating that these represented hyperphosphorylated species and that insoluble tau in JNPL3 mice consisted almost entirely of human tau. The 64 kD tau band observed in FTDP-17 and AD pathologic tau contains hyperphosphorylated 4R0N tau, the isoform expressed in the JNPL3 mice. This indicates that similar tau hyperphosphorylation occurs in both human tauopathies and in JNPL3 mice.

The development of NFT and similar motor dysfunction in an additional mouse line (JNPL+23) expressing P301L tau (4R2N) at two-fold higher levels than JNPL3 hemizygotes further demonstrates the impact of the P301L mutation on the development of tau pathology. In the JNPL+23 mice, exons 2, 3 and 10 are present.

Example 7

Transgenic Non-Human Mammals with Tangles and Amyloid Plaques: To further explore the development of the Tau pathology described above, and to determine the relationship between NFTs and mutant APP (and Aβ pathology), hemizygous JNPL3 mice were crossed with hemizygous transgenic mice expressing mutant $APP_{K670N,M671L}$, Tg2576. Tg2576 mice have markedly elevated Aβ levels at an early age and by 9–12 months develops extracellular AD-type Aβ deposits in the cortex and hippocampus. See, Hsiao et al, *Science,* 274:99 (1996) for a description of the Tg2576 mice. Mice were maintained on a SW/DBA2/C57B6 background. Mice were genotyped for the tau transgene by PCR between exons 1 and 5 of the human tau cDNA against an internal PS-2 control PCR (as described above) and genotyped for the APP transgene by PCR between A4 against an internal β-actin control PCR.

The brains and spinal cords of Tg2576×JNPL3 progeny, which included double mutant tau/mutant APP (termed "TAPP" mice), mutant tau, mutant APP, and non-transgenic mice at 9–10.5 months of age were compared for pathology, neuronal loss, insoluble tau, and Aβ levels. Immersion fixed (4% paraformaldehyde) paraffin embedded brain sections were immunostained with tau antibodies: MC-1 (Davies, 1:25–1:50), AT8 (1:5000) and AT180 (1:100) (Endogen); CP3 (Davies,1:100); CP9 (Davies, 1:100); CP13 (Davies, 1:100), PHF-1 (Davies, 1:100), Alz50 (Davies, 1:10), E-1 (Yen, 1:1000); ubiquitin: UH19 (Ksiezak-Reding, 1:500);

NFT antibody: Ab39 (Yen, 1:20); Ab69 (Yen, 1:20); TG# (1:10); GFAP (Biogenex, 1:100); and phosphorylated neurofilament (Sternberger-Meyer; SMI-31, 1:5000) using standard avidin or streptavidin biotin peroxidase methods. Paraffin embedded sections were used for histochemical stains (hematoxylin & eosin), thioflavin-S, Congo red, and silver stains.

Brain and spinal cord were dissected and immersion fixed in paraformaldehyde. For pre-embedding, immuno-EM was performed as described above. Immunolabeled areas were dissected, fixed in $OsO_4$, dehydrated and embedded in Epon. For post-embedding immuno-EM, small pieces of fixed tissue from brainstem and spinal cord were embedded in LR White resin. Primary tau antibodies (CP13) were used to stain ultrathin sections on nickel grids, followed by gold-conjugated secondary antibodies. For routine ultrastructural studies, tissues were immersion fixed in the same fixative for another 4 hr, followed by $OsO_4$ and uranyl acetate, then dehydrated and embedded in Epon.

Figure 4:
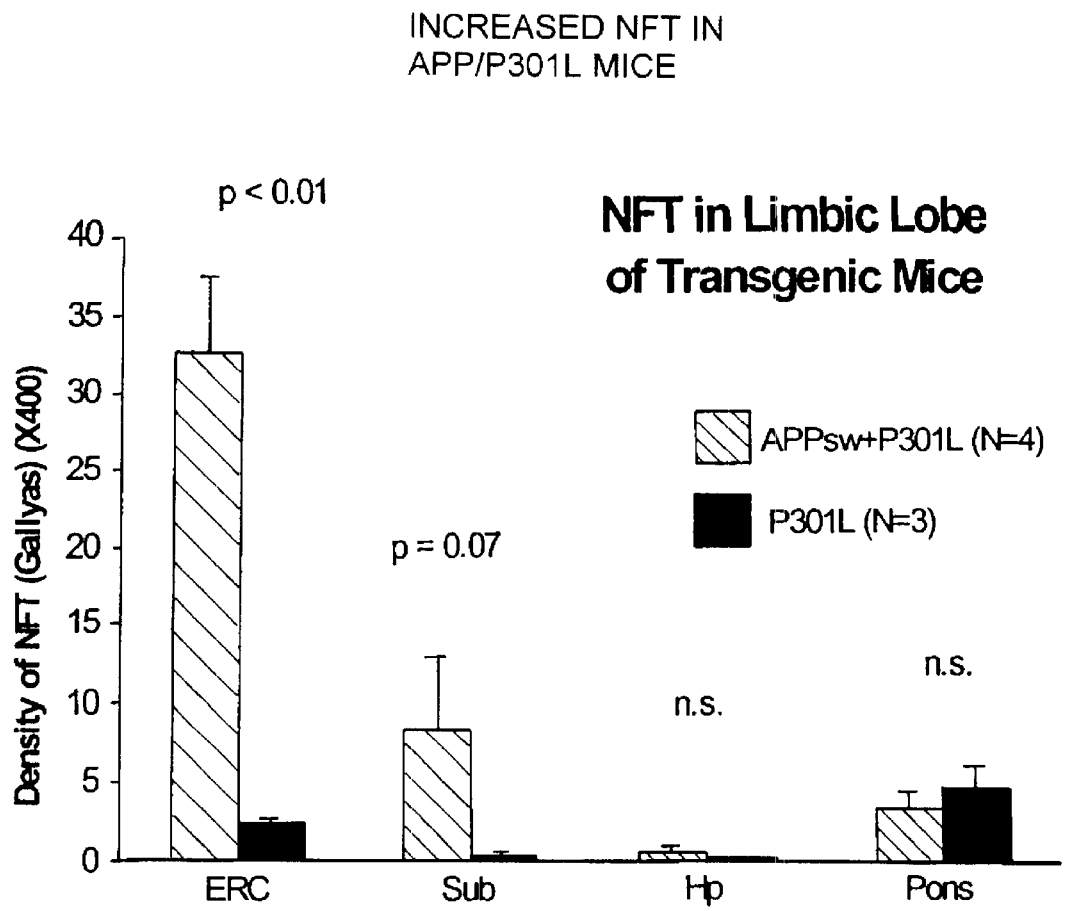
FIG. 4 is a graph of the density of neurofibrillary tangles in the limbic lobe of P301L or APP$_{sw}$+P301L transgenic mice.

Examination of the brain and spinal cord indicated that TAPP mice have amyloid plaques and, in addition, have markedly increased numbers and distribution of NFTs in the limbic area including the entorhinal cortex, amygdala, subiculum and hippocampus compared to single mutant tau mice (FIG. 4). The largest increases in NFT pathology were seen in the entorhinal cortex and subiculum [10 fold and 7 fold increases respectively ($p<0.01$)]. The number and distribution of pretangles also was increased, particularly in the cerebral cortex and hippocampus. The enhanced NFT pathology in the limbic regions correlates with the areas in which $A\beta$ pathology first develops in Tg2576 mice. A concomitant increase in gliosis (GFAP immunoreactivity) was observed in the vicinity of the NFTs and pretangles.

The spinal cord pathology was identical in the both the single mutant tau and double mutant TAPP transgenic mice, which exhibited widespread NFTs throughout the anterior horn, accompanied by motor neuron loss and gliosis. NFTs in both mutant tau/APP and mutant tau only mice stained with Thioflavin S, Congo red, Gallyas, Bodian and Bielchowsky silver stains and were immunoreactive with antibodies recognizing conformational (Ab39, Ab69, Alz50, MC-1), phosphorylated (AT8, AT180, CP3, CP9, CP13, PG5, PHF-1 and TG3) and non-phosphorylated (E1) tau epitopes. The number and distribution of $A\beta$ plaques was identical to that seen in age matched APP mutant i.e. the frontal, temporal, and entorhinal cortices and hippocampus as determined by Thioflavin S and Congo red staining. However, $A\beta42$ immunoreactivity was more prominent than $A\beta40$ in the plaques in the mutant TAPP mice and more tau positive dystrophic neurites were associated with the plaques compared to APP only littermates.

Ultrastructurally, the NFTs were composed of tau positive straight filaments 17–22 nm in diameter that sometimes form herring-bone structures similar to those described in Pick's disease. A large percentage of the cell volume was occupied by the tau positive filaments, which displaced the nucleus and compressed the Golgi apparatus.

Soluble tau levels in the mutant TAPP and mutant tau only brains were equivalent indicating there was no promoter interaction from the mouse prion promoter and the hamster prion promoter, which drives the tau and APP transgenes, respectively. Insoluble tau levels in the cortex/hippocampus were compared to the remainder of the forebrain/hindbrain. Insoluble tau levels were significantly increased in the mutant tau/APP cortex/hippocampus fraction compared to the single tau transgenics with significant accumulation of hyperphosphorylated species migrating at 64 kD. The elevated insoluble tau in the cortex and hippocampus fraction correlates with the enhanced NFT pathology seen in the entorhinal cortex and limbic system in the mutant tau/APP mice. As described above, the 64 kD band contains hyperphosphorylated tau of the same isoform, 4R0N, expressed by the tau transgene. In the single tau mutant mice, the majority of the insoluble tau was detected in the forebrain/hindbrain fraction where most of the tau pathology is observed in the tau only animals.

In additional to the enhanced NFT pathology in the mutant tau/APP mice, granulovacuolar degeneration was observed in hippocampal pyramidal cells characterized by vacuoles with eosinophilic dense cores, which are hypothesized to be associated with the sequestration of altered tau. See, Dickson et al., *Acta Neuropathol.*, 85:463 (1993). Some neurons had multiple granulovacuolar bodies. Occasionally, granulovacular degeneration was observed in mutant tau only mice and it appears that the extent of granulovacular degeneration was associated with the amount of tau pathology.

Figure 5:
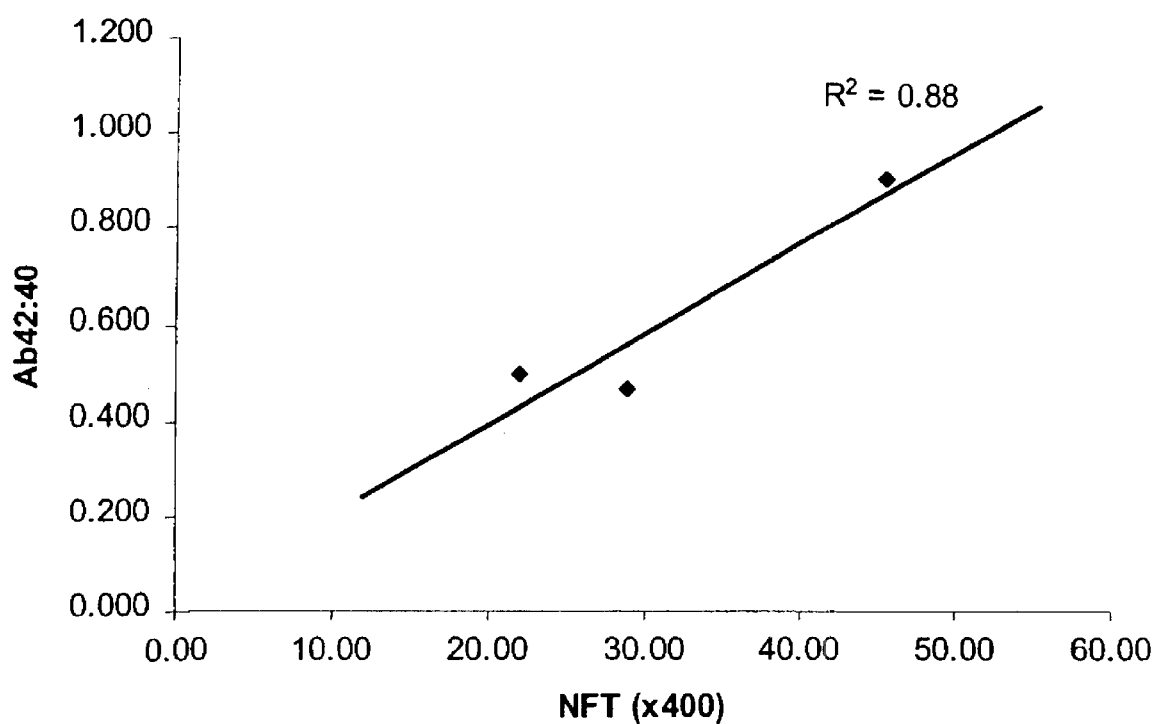
FIG. 5 is a graph of the ratio of Aβ42:Aβ40 vs. the number of entorhinal neurofibrillary tangles in APP$_{sw}$+P301L transgenic mice.

Brain $A\beta1-40$ and $A\beta1-42$ were compared in hemibrains from 9–10.5 month old mutant TAPP mice versus their APP only littermates using sandwich enzyme linked immunosorbent assays (ELISA) specific for human $A\beta$. See, Gravina et al., *J. Biol. Chem.*, 270:7013 (1995). Both $A\beta1-40$ and $A\beta1-42$ levels were elevated in the mutant TAPP brains compared to single transgenic APP littermates. The increased ratio of $A\beta42/A\beta40$ correlated with the number of NFTs in the entorhinal cortex (FIG. 5). Despite elevated $A\beta$ levels, there was no increase in the $A\beta$ plaque burden in the double mutant TAPP mice over APP only transgenic mice at the same age. This suggests that $A\beta$ environment, but not necessarily the formation of mature senile plaques, is responsible for the modulation and enhancement of the tau phenoytype in the double mutant TAPP mice.

Double mutant TAPP mice develop similar motor and behavioral disturbances as their singly transgenic tau littermates e.g. progressive hind limb weakness, dystonia, hunched posture, eye irritations, reduced vocalization, and grooming. The motor and behavioral phenotype is most likely associated with the spinal cord and muscular pathology that is essentially identical in the mutant TAPP and tau only mice. APP and non tg mice do not exhibit these behavioral and motor abnormalities. The double mutant animals provide evidence that APP or $A\beta$ can directly modulate the formation and deposition of tau NFTs.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A transgenic mouse comprising a nucleic acid construct, said construct comprising a regulatory element operably linked to a nucleic acid molecule encoding a human Tau polypeptide, wherein said polypeptide comprises a pathogenic Tau mutation at amino acid 301 and is expressed in the brain of said transgenic mouse, and wherein said transgenic mouse exhibits a Tau pathology.

2. The transgenic mouse of claim 1, wherein said regulatory element is a brain-specific promoter.

3. The transgenic mouse of claim 2, wherein said brain-specific promoter is a prion gene promoter.

4. The transgenic mouse of claim 1, wherein said mutation is a substitution of a leucine residue for a proline residue at amino acid 301.

5. The transgenic mouse of claim 1, wherein said mouse develops neurofibrillary tangles.

6. Progeny of the transgenic mouse of claim 1, wherein said progeny comprise said nucleic acid construct.

7. A transgenic mouse comprising:

(a) a first nucleic acid construct comprising a regulatory element operably linked to a nucleic acid molecule encoding a human Tau polypeptide, wherein said polypeptide comprises a pathogenic Tau mutation at amino acid 301 and is expressed in the brain of said transgenic mouse; and (b) a second nucleic acid construct comprising a regulatory element operably linked to a nucleic acid molecule encoding a human amyloid precursor protein (APP), wherein said human APP comprises a mutation at amino acids 670 and 671, and wherein said transgenic mouse exhibits a Tau pathology.

8. The transgenic mouse of claim 7, wherein an asparagine residue is substituted at amino acid 670 and a leucine residue is substituted at amino acid 671.

9. The transgenic mouse of claim 7, wherein said transgenic mouse develops neurofibrillary tangles and amyloid plaques.

10. The transgenic mouse of claim 7, wherein said mouse develops an increased number of neurofibrillary tangles as compared with a control transgenic mouse expressing a mutant Tau polypeptide.

11. Progeny of the transgenic mouse of claim 7, wherein said progeny comprise said first nucleic acid construct and said second nucleic acid construct.

12. A method for identifying agents that inhibit development of a Tau pathology, said method comprising administering a test agent to a transgenic mouse, said transgenic mouse comprising a nucleic acid construct, said construct comprising a regulatory element operably linked to a nucleic acid molecule encoding a human Tau polypeptide, wherein said polypeptide comprises a pathogenic Tau mutation at amino acid 301 and is expressed in the brain of said transgenic mouse, and wherein said transgenic mouse exhibits a Tau pathology, and determining if said test agent inhibits development of said Tau pathology in said transgenic mouse as compared with a corresponding transgenic mouse to which said test agent has not been administered.

13. The method of claim 12, wherein said transgenic mouse develops neurofibrillary tangles.

14. The method of claim 12, wherein said transgenic mouse further comprises a second nucleic acid construct, said second nucleic acid construct comprising a regulatory element operably linked to a nucleic acid molecule encoding a human APP, wherein said human APP comprises a mutation at amino acids 670 and 671.

15. The method of claim 14, wherein an asparagine residue is substituted at amino acid 670 and a leucine residue is substituted at amino acid 671.

16. The method of claim 14, wherein said transgenic mouse develops neurofibrillary tangles and amyloid plaques.

17. The method of claim 14, wherein said mouse develops an increased number of neurofibrillary tangles as compared with a control transgenic mouse expressing a mutant Tau polypeptide.

* * * * *

UNITED STATES PATENT AND TRADEMARK OFFICE
CERTIFICATE OF CORRECTION

PATENT NO. : 6,664,443 B1
DATED : December 16, 2003
INVENTOR(S) : Michael L. Hutton, Jada M. Lewis and Eileen M. McGowan It is certified that error appears in the above-identified patent and that said Letters Patent is hereby corrected as shown below:

<u>Title page,</u>
Item [56], References Cited, OTHER PUBLICATIONS, please delete "466" and insert -- 446 -- therefor.

Signed and Sealed this

Thirty-first Day of August, 2004

JON W. DUDAS
*Director of the United States Patent and Trademark Office*

UNITED STATES PATENT AND TRADEMARK OFFICE
CERTIFICATE OF CORRECTION

PATENT NO. : 6,664,443 B1
DATED : December 16, 2003
INVENTOR(S) : Michael L. Hutton, Jada M. Lewis and Eileen M. McGowan It is certified that error appears in the above-identified patent and that said Letters Patent is hereby corrected as shown below:

Title page,
Item [75], Inventors, "Michael L. Hutton", please delete "US" and insert -- UK -- therefor; and "Eileen M. McGowan", please delete "US" and insert -- UK -- therefor.

Signed and Sealed this

Twenty-third Day of November, 2004

JON W. DUDAS
*Director of the United States Patent and Trademark Office*

SEQUENCE LISTING

<160> NUMBER OF SEQ ID NOS: 13

<210> SEQ ID NO 1
<211> LENGTH: 19
<212> TYPE: DNA
<213> ORGANISM: Artificial Sequence
<220> FEATURE:
<223> OTHER INFORMATION: primer

<400> SEQUENCE: 1
atcgcagcgg ctacagcag                                                19

<210> SEQ ID NO 2
<211> LENGTH: 21
<212> TYPE: DNA
<213> ORGANISM: Artificial Sequence
<220> FEATURE:
<223> OTHER INFORMATION: primer

<400> SEQUENCE: 2
tggtttatga tggatgttgc c                                             21

<210> SEQ ID NO 3
<211> LENGTH: 19
<212> TYPE: DNA
<213> ORGANISM: Artificial Sequence
<220> FEATURE:
<223> OTHER INFORMATION: primer

<400> SEQUENCE: 3
tcttggcttt ggcgttctc                                                19

<210> SEQ ID NO 4
<211> LENGTH: 31
<212> TYPE: PRT
<213> ORGANISM: Homo sapiens

<400> SEQUENCE: 4

Val Gln Ile Ile Asn Lys Lys Leu Asp Leu Ser Asn Val Gln Ser Lys
 1               5                  10                  15

Cys Gly Ser Lys Asp Asn Ile Lys His Val Pro Gly Gly Gly Ser
            20                  25                  30

<210> SEQ ID NO 5
<211> LENGTH: 31
<212> TYPE: PRT
<213> ORGANISM: Homo sapiens

<400> SEQUENCE: 5

Val Gln Ile Val Ser Lys Lys Val Ser Tyr Ser His Ile Gln Ser Lys
 1               5                  10                  15

Cys Gly Ser Lys Asp Asn Ile Lys His Val Pro Gly Gly Gly Asn
            20                  25                  30

<210> SEQ ID NO 6
<211> LENGTH: 31
<212> TYPE: PRT
<213> ORGANISM: Rattus norvegicus

<400> SEQUENCE: 6

Val Arg Ile Leu Asn Lys Lys Met Asp Phe Ser Lys Val Gln Ser Arg
 1               5                  10                  15

-continued

Cys Gly Ser Lys Asp Asn Ile Lys His Ser Ala Gly Gly Gly Asn
            20                  25                  30

<210> SEQ ID NO 7
<211> LENGTH: 30
<212> TYPE: PRT
<213> ORGANISM: Caenorhabditis elegans

<400> SEQUENCE: 7

Val Glu Ile Phe Ser Glu Lys Arg Leu Tyr Asn Ala Gln Ser Lys Val
 1               5                  10                  15

Gly Ser Leu Lys Asn Ala Thr His Val Ala Gly Gly Asn
            20                  25                  30

<210> SEQ ID NO 8
<211> LENGTH: 22
<212> TYPE: RNA
<213> ORGANISM: Homo sapiens

<400> SEQUENCE: 8
cagugugagu accuucacac gu                                        22

<210> SEQ ID NO 9
<211> LENGTH: 11
<212> TYPE: RNA
<213> ORGANISM: Homo sapiens

<400> SEQUENCE: 9
guccauucau a                                                    11

<210> SEQ ID NO 10
<211> LENGTH: 18
<212> TYPE: DNA
<213> ORGANISM: Artificial Sequence
<220> FEATURE:
<223> OTHER INFORMATION: Synthetically generated oligonucleotides

<400> SEQUENCE: 10
aacacgtcct gggaggcg                                             18

<210> SEQ ID NO 11
<211> LENGTH: 35
<212> TYPE: DNA
<213> ORGANISM: Artificial Sequence
<220> FEATURE:
<223> OTHER INFORMATION: Synthetically generated oligonucleotides

<400> SEQUENCE: 11
ccgcgagacc caccttgga ggctccagat ttatc                           35

<210> SEQ ID NO 12
<211> LENGTH: 34
<212> TYPE: DNA
<213> ORGANISM: Artificial Sequence
<220> FEATURE:
<223> OTHER INFORMATION: Synthetically generated oligonucleotides

<400> SEQUENCE: 12
ctttcaggcc agcgtccgtg tcaccctctt ggtc                           34

<210> SEQ ID NO 13
<211> LENGTH: 35
<212> TYPE: DNA
<213> ORGANISM: Artificial Sequence
<220> FEATURE:

-continued

```
<223> OTHER INFORMATION: Synthetically generated oligonucleotides

<400> SEQUENCE: 13
tttgtcatcg cttccagtcc cgtctttgct tttac                                    35
```